US006489357B1

(12) United States Patent
Eterovic et al.

(10) Patent No.: US 6,489,357 B1
(45) Date of Patent: Dec. 3, 2002

(54) TOBACCO CEMBRANOIDS BLOCK THE EXPRESSION OF THE BEHAVIORAL SENSITIZATION TO NICOTINE AND INHIBIT NEURONAL ACETYLCHOLINE RECEPTORS

(75) Inventors: Vesna A. Eterovic, Rio Piedras, PR (US); Pedro A. Ferchmin, Rio Piedras, PR (US); Richard M. Hann, Guaynabo, PR (US); One R. Pagan, Ithaca, NY (US); Abimael D. Rodriguez, Rio Piedras, PR (US); Osvaldo Rosario, Rio Piedras, PR (US)

(73) Assignees: University of Puerto Rico, San Juan, PR (US); Universidad Central del Caribe Bayamòn, PR (US)

( * ) Notice: Subject to any disclaimer, the term of this patent is extended or adjusted under 35 U.S.C. 154(b) by 0 days.

(21) Appl. No.: 09/693,431

(22) Filed: Oct. 21, 2000

Related U.S. Application Data

(63) Continuation-in-part of application No. 09/092,407, filed on Jun. 4, 1998, now Pat. No. 6,204,289.
(60) Provisional application No. 60/224,659, filed on Aug. 11, 2000.

(51) Int. Cl.⁷ ..................... A61K 31/045; A61K 31/215
(52) U.S. Cl. ................. 514/451; 514/460; 514/461; 514/470; 514/475; 514/813
(58) Field of Search ................. 514/451, 460, 514/461, 470, 475, 813

(56) References Cited

U.S. PATENT DOCUMENTS

| | | | |
|---|---|---|---|
| 4,789,640 A | | 12/1988 | Lindstrom |
| 4,835,162 A | * | 5/1989 | Abood ................. 514/305 |
| 4,906,794 A | | 3/1990 | Umezu et al. |
| 5,039,671 A | | 8/1991 | Baggiolini et al. |
| 5,041,389 A | | 8/1991 | Lindstrom |
| 5,248,690 A | | 9/1993 | Caldwel et al. |
| 5,278,176 A | | 1/1994 | Lin et al. |
| 5,399,575 A | | 3/1995 | Friebe et al. |
| 5,418,229 A | | 5/1995 | Alker et al. |
| 5,591,590 A | | 1/1997 | Heinemann et al. |
| 5,594,011 A | | 1/1997 | McDonald et al. |
| 5,599,709 A | | 2/1997 | Lindstrom et al. |
| 6,204,289 B1 | * | 3/2001 | Eterovic et al. ............ 514/451 |

FOREIGN PATENT DOCUMENTS

| | | |
|---|---|---|
| EP | 0 258 082 | 3/1998 |
| EP | 0 271 387 | 3/1998 |

OTHER PUBLICATIONS

V. A. Eterovic—*Caribbean Cembranoids are Noncompetitive Inhibitors of the Nicotinic Acetylcholine Receptors*—Abstract No. 52—1991.

V. A. Eterovic—*Cembranoids from Eunicea: A New Group of Noncompetitive Inhibitors of the Nicotinic Acetylcholine Receptor* (AchR)—Abstract No. 53—1992.

V. A. Eterovic—*Differences in the Action of Noncompetitive Inhibitors of Muscle and Electric Organ Acetylcholine Receptors*—Abstract No. 55—1992.

O. R. Pagan, et al.—*Inhibition of [³H] Phencyclidine Binding to the Nicotinic Acetylcholine Receptor by Cembranoids from Gorgonians*—Abstract Bi, 59—1992.

R. M. Hann, et al.—*The Acetylcholine Receptor: Binding Sites for Competitive and Noncompetitive Inhibitors*—Abstract No. 60—1993.

Vesna A. Eterovic, et al.—*Diterpenoids from Caribbean Gorgonians Act as Noncompetitive Inhibitors of the Nicotinic Acetylcholine Receptor*—Cellular and Molecular Neurobiology, vol. 13, No. 2, 1993, pp. 99–110.

V. A. Eterovic, et al.—*The Ion Channel of Muscle and Electric Organ Acetylcholine Receptors; Differing Affinities for Noncompetitive Inhibitors*—Cellular and Molecular Neurobiology, vol. 13, No. 1, 1993, pp. 111–121.

R. M. Hann, et al.—*The Biological Actions of Gorgonian Cembranoids on the Central Nervous System and the Peripheral Acetylcholine Receptor*—Abstract No. 62—1993.

V. A. Eterovic, et al.—*Effect of Cembranoids on Neuronal Acetylcholine Receptors*—Abstract No. 65—1993.

R. Lu, et al.—*New Cembranoid Inhibitors or the Nicotinic Acetylcholine Receptor: Structure–Function Relationships*—Abstract No. 66—1993.

R. M. Hann, et al.—*The Biological Actions of Gorgonian Cembranoids on the Central Nervous System and the Peripheral Acetylcholine Receptor*—Abstract—1993.

R. M. Hann, et al.—*Further Characterization of how Cembranoids Inhibit the Acetylcholine Receptor*—Abstract No. 73—1994.

Vesna Ana Eterovic, et al.—*Cembranoids Inhibit Neuronal Acetylcholine Receptors*—Abstract—Society for Neuroscience—1994.

Richard M. Hann, et al.—*The a–Conotoxins GI and MI Distinguish between the Nicotinic Acetylcholine Receptor Agonist Sites while SI Does Not*—Article—Biochemistry Magazine—1994.

R. M. Hann, et al.—*Affinities of Gorgonian Cembranoids for the Phencyclidine High–Affinity Binding Site on the Nicotinic Acetylcholine Receptor*—Abstract No. 80—1995.

(List continued on next page.)

Primary Examiner—Frederick Krass
(74) Attorney, Agent, or Firm—Patent Law Offices of Heath W. Hoglund

(57) ABSTRACT

The subject invention relates the use of cembranoids to inhibit nicotine addiction at the behavioral level. The subject host is sensitized to nicotine. Cembranoids are then administered to reduce such sensitization.

16 Claims, 1 Drawing Sheet

OTHER PUBLICATIONS

R. M. Hann, et al.—*The Gorgonian Cembranoid Binding Site on the Nicotinic Acetylcholine Receptor*—Abstract No. 81—1995.

V. A. Eterovic—*The Nicotinic Acetylcholine Receptor: Inhibitor Tales*—Abstract No. 83—1995.

R. M. Hann, et al.—*Affinities of New Cembranoids for the Nicotinic Acetylcholine Receptor*—Abstract No. 86—Society for Neuroscience—1995.

O. R. Pagan, et al.—*Inhibition of [$^3$H]—Phencyclidine Binding to the Nicotinic Acetylcholine Receptor by Gorgonian–derived Diterpenoids*—Abstract No. 88—1995.

Vesna A. Eterovic, et al.—Neuroscience Research—*Noncompetitive Inhibitors of the Acetylcholine Receptor Help Paint a Picture of its Ion Channel*—PRHSJ vol. 14, No. 3, Sep., 1995, pp. 199–209.

R.M. Hann, et al.—*Gorgonian Cembranoids from Puerto Rico as Noncompetitive Inhibitors of the Nicotinic Acetylcholine Receptor*—Abstract No. 89—1996.

Richard M. Hann, et al. —*Hydrophobicity as an Affinity Factor for Cembranoid Binding to the Nicotinic Acetylcholine Receptor*—Abstract No. 95—1996.

V. A. Eterovic, et al.—*The Noncompetitive Inhibitors Domain of the Nicotinic Acetylcholine Receptor*—Abstract—1997.

Misty Jeanne Eaton, et al.—*βT10'A and βT10'I Mutations in the M2 Region of Nicotinic Receptors Alter the Potency of Phencyclidine, but not Cembranoid Pseudoplexauric Acid Methyl Ester.*—Abstract No. 16—1998.

Y. Nicolau, et al.—*Behavioral Effects of Cembranoids: Evidence of In Vivo Central Nicotinic Action*—Abstract No. 25—1998.

Oné R. Pagán, et al. —*A Model for the Relationship between the Local Anesthetic, General Anesthetic and Cembranoid Binding Sites on the Torpedo Nicotinic Acetylcholine Receptor*—Abstract No. 26—1998.

Richard M. Hann, et al.—*Characterization of Cembranoid Interaction with the Nicotinic Acetylcholine Receptor*—The Journal of Pharmacology and Experimental Therapeutics—1998—pp. 253–260.

P. A. Ferchmin, et al—*Coral and Tobacco Cembranoids Inhibit the Expression of Nicotine Sensitization of Exploratory Activity in Rats*—Abstract—1999.

Oné Reynaldo Pagán, et al. —*Mutually Exclusively Binding of Anesthetic Agents and Gorgonian Cembranoids to the Nicotinic Acetylcholine Receptor*—Abstract—1998.

Database WPI, Section Ch. Week 9533, Derwent Publications Ltd., London, GP; AN 95–248365, XP–002080455 (Abstract) 1997.

Hahn R. M., et al.—*Characterization of cembranoid interaction with the nicotinic acetylcholine receptor.* J. Pharmac. Exp. Ther. 287:253–260., 1998.

Pagan, O. R., et al.—*Effect of cembranoids and anesthetic agents on [$^3$H]–tenocyclidine binding to the nicotinic acetylcholine receptor from Torpedo Californica*, M. S. Tesis, University of Puerto Rico, Medicinal Sciences Campus, San Juan, Puerto Rico; 1998.

Picciotto M., et al.—Acetylcholine receptors containing the β2 subunit are involved in the reinforcing properties of nicotine. Nature, 391: 173–177, 1998.

Biello, M., et al.—*Determination of Cembranoids in Cigarette Smoke*—Eighth Puerto Rico Neuroscience Conference, San Juan, Puerto Rico—Abstract #113—1999.

Clementi, F., et al.—*Neuronal nicotinic acetylcholine receptors: from structure to therapeutics*—TiPS 21:35–37—2000.

Ferchmin, P.A., et al. —*Tobacco Cembranoids Block Behavioral Sensitization to Nicotine and Inhibit Neuronal Acetylcholine Receptor Function*—Journal of Neuroscience Research 64:18–25—2001.

* cited by examiner

TOBACCO CEMBRANOIDS BLOCK THE EXPRESSION OF THE BEHAVIORAL SENSITIZATION TO NICOTINE AND INHIBIT NEURONAL ACETYLCHOLINE RECEPTORS

This application is a continuation-in-part of U.S. patent application Ser. No. 09/092,407, filed Jun. 4, 1998 and now U.S. Pat. No. 6,204,289, and claims the benefit of U.S. provisional application No. 60/224,659, filed Aug. 11, 2000, both of which are incorporated herein by reference.

FEDERALLY SPONSORED RESEARCH

The inventions claimed herein were made with Government support, including grants GM50695, GM52277, NS39408 and G-12RR03035, and the Government has certain rights in the inventions.

BACKGROUND

Despite the consensus that nicotine is the compound responsible for the addictive properties of cigarettes, other factors may contribute to this addiction. Besides nicotine, tobacco contains thousands of other compounds among which there is a family of cyclic diterpenoids called cembranoids. Cyclic diterpenoids are also found in marine invertebrates, specifically Gorgonian species (soft corals).

Cembranoids are found in both tobacco leaves and flowers. Their content varies considerably with the tobacco species, constituting on the average about 1% (w/w) of green leaves. By comparison, nicotine content in cigarette tobacco is about 1–3%. The most abundant tobacco cembranoids are (1S,2E,4R,6R,7E,11E)-cembra-2,7,11-triene-4,6-diol (also termed 4R-cembratriene) and its diasteroisomer (1S,2E,4S,6R,7E,11E)-cembra-2,7,11-triene-4,6-diol (also termed 4S-cembratriene). Both of these compounds are shown in FIG. 1. These compounds are thought to be the precursors of most of the over seventy currently known tobacco cembranoids. Relatively few biological effects of tobacco cembranoids have been described. These few described biological effects include regulation of plant growth, inhibition of tumor growth, inhibition of aldose reductase and of prostaglandin synthesis.

SUMMARY OF THE INVENTION

According to another aspect of the invention, administering cembranoids to a living host reduces sensitization to nicotine.

According to further aspects of the invention, the living host is sensitized to nicotine by regular administration of nicotine to the living host. The cembranoids are administered after the regular administration of nicotine to the living host. The cembranoids may all be the same compound or may be a plurality of different compounds, including eunicin, eupalmerin acetate, 12,13-bisepieupalmerin, 4S-cembratriene and 4R-cembratriene.

According to one aspect of the invention, the cembranoids are administered in a dose of approximately six milligrams of cembranoid per kilogram of host.

According to another aspect of the invention, the cembranoid is administered in a dose of approximately, or that does not exceed, a milligram of cembranoid per kilogram of host.

According to still further aspects of the invention, the living host is a mammal.

DETAILED DESCRIPTION OF THE INVENTION

Figure 1A:
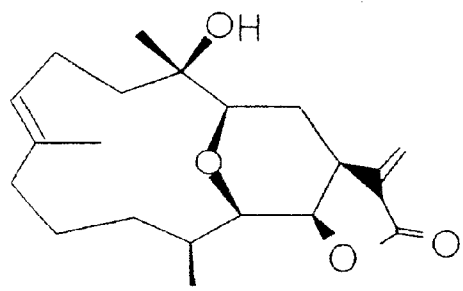
FIG. 1 depicts the structures of some of the cembranoids of the invention. These include: (A) eunicin; (B) eupalmerin acetate; (C) 12,13-bisepieupalmerin; (D) 1S,2E,4R,6R,7E,11E)-cembra-2,7,11-triene-4,6-diol; and (E) (1S,2E,4S,6R,7E,11E)-cembra-2,7,1 1 -triene-4,6-diol.
Figure 1B:
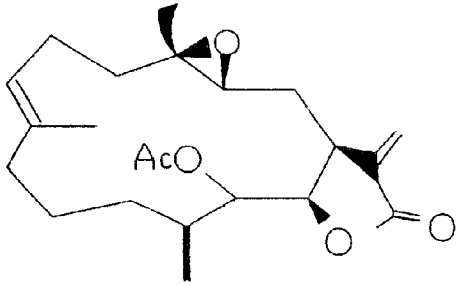
Figure 1C:
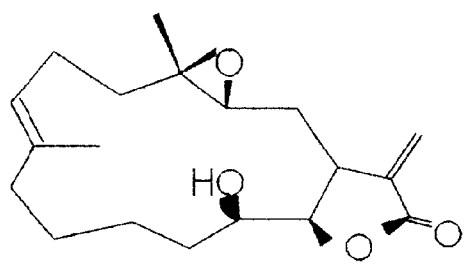
Figure 1D:
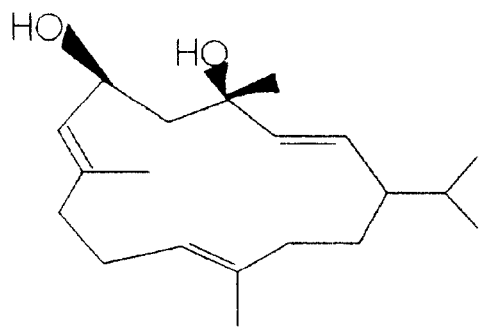
Figure 1E:
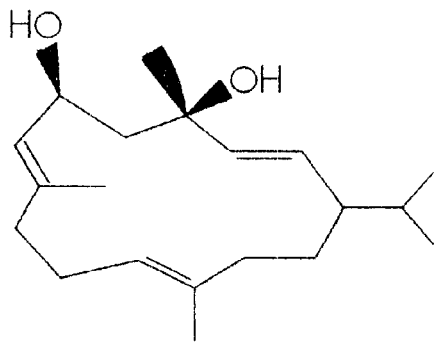

We have discovered that cembranoids inhibit nicotine addiction at the behavioral level. Thus, the administration of cembranoids may be used to block the behavioral sensitization to nicotine in living organisms. The administration of such compounds does not cause any immediate adverse health consequences to the subject host.

In one group of tests, rats were exposed and sensitized to nicotine. Specifically, the rats were injected with 0.3 mg/kg or 0.4 mg/kg of nicotine and tested on the Greek cross maze. The Greek cross maze is a maze shaped like a cross that contains a central gray compartment which connects to two black compartments on opposite sides and two white compartments on the remaining sides.

After the rats were sensitized, they were injected with one of the following: saline, nicotine, or a preinjection of at least one cembranoid 30 minutes before injecting them with nicotine, chosen as a result of which experimental group each rat belonged to. Immediately after one of the injections was administered to the rats, they were placed in the Greek cross maze for observation and analysis of locomotor activity. The rats were placed in the gray area and the times each rat fully entered or partially (both front paws and head) entered the black and white compartments were recorded for 10 minutes.

The rats that were injected with nicotine, for the first time, showed loss of control of voluntary muscle movement. One group of rats was injected with nicotine once a day for 6 days, and on the seventh day they were injected with a saline control solution. Another group had the rats injected with at least on cembranoid before being injected with the nicotine. Those injected with the saline solution did not express sensitization to nicotine. Those that were preinjected with at least one cembranoid showed a response similar to that observed after saline, thus no expression.

The specific test results will now be described in further detail.

EXAMPLE 1

First, cembranoids, when administered alone, do not effect the behavior of rats as measured on the Greek Cross maze. To show this we injected rats with DMSO and with cembranoids dissolved in DMSO. The activity of both groups of rats did not exhibit any significant differences. The specific results for a five-minute period are shown in the following table (Table I):

TABLE I

| Exp. # | Treatment | Total entries | N |
|---|---|---|---|
| 1 | Eunicin-2 mg/kg | 14.4 ± 0.7 | 9 |
|   | DMSO | 15.1 ± 0.7 | 9 |
| 2 | Eunicin-6 mg/kg | 16.7 ± 0.9 | 13 |
|   | DMSO | 16.5 ± 0.8 | 13 |
| 3 | Eunicin-2 mg/kg | 16.1 ± 0.7 | 9 |
|   | Eunicin-15 mg/k | 17.9 ± 1.1 | 9 |
|   | DMSO | 16.1 ± 0.7 | 9 |
| 4 | Eunicin-6 mg/kg | 17.2 ± 0.7 | 11 |
|   | DMSO | 17.0 ± 1.0 | 11 |

TABLE I-continued

| Exp. # | Treatment | Total entries | N |
|---|---|---|---|
| 5 | EUAC-2 mg/kg | 18.8 ± 1.2 | 11 |
| | EUAC-0.5 mg/kg | 16.2 ± 1.0 | 11 |
| | DMSO | 16.7 ± 1.0 | 11 |

The above table lists the results for five trials, as identified by the column titled "Exp. #." The column tilted "Treatment" identifies the type and dose of a cembranoid that was administered to the rats. EUAC is Eupalmerin Acetate. The column titled "Total Entries" lists the mean and ±s.e.m. of entries for each group. The column titled "N" lists the number of rats used. EXAMPLE 2

After sensitizing rats to nicotine as discussed above, the locomotor activity in the Greek cross maze was again measured, this time for a ten minute period. Marine cembranoids were administered to decrease the expression of sensitization to nicotine. The following table (Table II) illustrates the results:

TABLE II

| Exp. # | Days | Drug treatment | Total entries |
|---|---|---|---|
| 1 | 15 | Nicotine | 25.0 ± 3.1 |
| | 16 | Saline control | 13.5 ± 3.2 |
| | 30 | Nicotine | 23.7 ± 2.3 |
| | 62 | Nicotine | 24.0 ± 3.1 |
| | 64 | Eunicin + Nicotine | 17.0 ± 4.0 |
| 2 | 14 | Nicotine | 33.6 ± 2.1 |
| | 15 | Saline control | 22.4 ± 2.5 |
| | 22 | Nicotine | 35.8 ± 3.2 |
| | 28 | Eunicin + Nicotine | 26.9 ± 2.1 |
| | 30 | Eupalmerin Acetate + Nicotine | 26.8 ± 2.0 |
| 3 | 13 | Nicotine | 36.8 ± 2.1 |
| | 15 | Eunicin + nicotine | 28.5 ± 2.9 |
| | 29 | Eupalmerin Acetate + Nicotine | 27.8 ± 2.2 |

The above table lists the results for three different trials, as identified by the column titled "Exp. #." The locomotor activity was measured at various days after the initiation of the sensitization treatment as indicated in the column titled "Days." The column titled "Drug Treatment" identifies the drug(s) injected before measuring the locomotor activity. The doses used were: nicotine, 0.2 mg/Kg in exp. 1 and 0.3 mg/Kg in experiments 2 and 3; eunicin and eupalmerin acetate, 6 mg/Kg. The column titled "Total Entries" lists the mean and ±s.e.m. of entries measured on the Greek cross maze for each group. In experiments 1 and 2, the activity observed after injecting saline solution provides a negative control (where sensitization is not expressed) to which the values from the other treatments are compared; in experiment 3, the activity observed after injection of nicotine (day 13) provides a positive control (100% expression of sensitization) for comparison with the other treatments.

EXAMPLE 3

Again, after sensitizing rats to nicotine as discussed above, the locomotor activity in the Greek cross maze was measured. A tobacco cembranoid was administered to reduce the sensitization to nicotine. Mecamylamine (MCA) was also administered and its effect measured. The following table (Table III) illustrates the results:

TABLE III

| Days | Drug treatment | Total entries |
|---|---|---|
| 11 | Nicotine | 38.2 ± 3.0 |
| 12 | MCA + Nicotine | 26.7 ± 2.3 |
| 13 | Nicotine | 41.0 ± 2.8 |
| 18 | Nicotine | 42.7 ± 4.8 |
| 19 | Saline control | 23.6 ± 1.8 |
| 20 | Nicotine | 39.6 ± 4.4 |
| 21 | 4R-Cembratriene + Nicotine | 23.0 ± 4.5 |
| 22 | Nicotine | 41.7 ± 3.5 |

For the above table, the locomotor activity was measured at various days after the initiation of the sensitization treatment as indicated in the column titled "Days." The column titled "Treatment" identifies the drug(s) injected before measuring the locomotor activity. The dose of 4R-cembratriene, also termed (1S,2E,4R,6R,7E)-CEMBRA-2,7,11-TRIENE-4,6-DIOL, was 6 mg/kg. The activity of day 19, after saline injection, provides a control measurement in which expression of sensitization is absent.

The following references are hereby expressly incorporated by reference in their entirety.

U.S. patent application Ser. No. 09/092,407, filed Jun. 4, 1998; now U.S. Pat. No. 6,204,289;

U.S. Provisional Patent Application No. 60/224,659, filed Aug. 11, 2000;

Biello M. Pagán O. R., Cortés S., Rosario O., Ferchmin P. A. and Eterovic V. A. (1999). Determination of cembranoids in cigarette smoke. Eight Puerto Rico Neuroscience Conference (San Juan, Puerto Rico);

Clementi F., Fornasari D., Gotti C., 2000 Neuronal nicotinic acetylcholine receptors: from structure to therapeutics. TiPS 21:35–37;

Hann R. M., Pagán O. R., Gregory L., Jácome T., Rodriguez A. D., Ferchmin P. A., Lu R., and Eterovic V. A. (1998) Characterization of cembranoid interaction with the nicotinic acetylcholine receptor. J.Pharmac.Exp. Ther. 287:253–260;

Pagán O. R. (1998) Effect of cembranoids and anesthetic agents on [$^3$H]-tenocyclidine binding to the nicotinic acetylcholine receptor from Torpedo californica. M.S. Thesis, University of Puerto Rico Medical Sciences Campus, San Juan, Puerto Rico;

Picciofto M., Zoli M., Rimondini R., Léna C., Marubio L. M., Merlo Pich E., Fuxe K. and Changeux, J.-P. (1998) Acetylcholine receptors containing the β2 subunit are involved in the reinforcing properties of nicotine. Nature, 391:173–177; and Ferchmin P. A., Lukas R. J., Hann R. M., Fryer J. D., Eaton J. B., Pagan O. R., Rodriguez A. D., Nicolau Y., Rosado M., Cortes S. and Eterovic V. A., (2000) Tobacco Cembranoids Block the Expression of the Behavioral Sensitization to Nicotine and Inhibit Neuronal Acetylcholine Receptors. Submitted for publication to Journal of Neuronal Science Research (copy attached as Appendix A.)

The above general and detailed descriptions are exemplerary only and are intended to provide further explanation of the invention as claimed. Of course those skilled in the art will appreciate many modifications that may be made without departing from the scope and spirit of the invention. The following claims are intended to encompass all such modifications.

We claim:

1. A method of reducing sensitization to nicotine in a living host by:
   administering nicotine to the living host so that the living host becomes sensitized to nicotine; and
   administering at least one cembranoid to the living host to reduce the sensitization to nicotine.

2. The method of claim 1, wherein the step of administering the at least one cembranoid further comprises administering nicotine along with the at least one cembranoid to the living host.

3. The method of claim 1, further comprising the step of administering nicotine to the living host after administering the at least one cembranoid to the living host.

4. The method of claim 1, wherein the living host is a mammal.

5. The method of claim 1, wherein administering the at least one cembranoid to the living host comprises administering a plurality of different cembranoids.

6. The method of claim 1, further comprising the step of selecting the cembranoid from the group consisting of:
   EUNICIN;
   EUPALMERIN ACETATE;
   12,13-BISEPIEUPALMERIN;
   (1S,2E,4S,6R,7E,11E)-CEMBRA-2,7,11-TRIENE-4,6-DIOL; and
   (1S,2E,4R,6R,7E,11E)-CEMBRA-2,7,11-TRIENE-4,6-DIOL.

7. The method of claim 1, wherein the step of administering at least one cembranoid comprises administering a dose that does not exceed six milligrams of cembranoid per kilogram of host.

8. The method of claim 1, wherein the step of administering at least one cembranoid comprises administering a dose of approximately a milligram of cembranoid per kilogram of host.

9. The method of claim 1, wherein the step of administering at least one cembranoid comprises administering a dose of less than one milligram of cembranoid per kilogram of host.

10. A method of reducing sensitization to nicotine in a living host that has become sensitized to nicotine comprising the step of administering at least one cembranoid to the living host to reduce the sensitization to nicotine in a dose that does not exceed six milligrams of cembranoid per kilogram of host.

11. The method of claim 9, wherein the step of administering the at least one cembranoid further comprises administering a dose of less than 0.5 milligrams of cembranoid per kilogram of host.

12. The method of claim 10, wherein the step of administering the at least one cembranoid comprises administering EUNICIN.

13. The method of claim 10, wherein the step of administering the at least one cembranoid comprises administering EUPALMERIN ACETATE.

14. The method of claim 10, wherein the step of administering the at least one cembranoid comprises administering 12,13-BISEPIEUPALMERIN.

15. The method of claim 10, wherein the step of administering the at least one cembranoid comprises administering (1S,2E,4S,6R,7E,11E)-CEMBRA-2,7,11-TRIENE-4,6-DIOL.

16. The method of claim 10, wherein the step of administering the at least one cembranoid comprises administering (1S,2E,4R,6R,7E,11E)-CEMBRA-2,7,11-TRIENE-4,6-DIOL.

* * * * *